(12) United States Patent
Testani et al.

(10) Patent No.: US 8,128,549 B2
(45) Date of Patent: Mar. 6, 2012

(54) CAPACITOR FAILURE DETECTION

(75) Inventors: Anthony Testani, Conshohocken, PA (US); Mark Edward Riehl, Doylestown, PA (US); Frank C. Klingshirn, Medina, OH (US)

(73) Assignee: Neuronetics, Inc., Malvern, PA (US)

( * ) Notice: Subject to any disclaimer, the term of this patent is extended or adjusted under 35 U.S.C. 154(b) by 1304 days.

(21) Appl. No.: 11/676,571

(22) Filed: Feb. 20, 2007

(65) Prior Publication Data
US 2008/0200748 A1 Aug. 21, 2008

(51) Int. Cl.
*A61N 1/00* (2006.01)
(52) U.S. Cl. .......................................... 600/13
(58) Field of Classification Search .................. 600/9–15
See application file for complete search history.

(56) References Cited

U.S. PATENT DOCUMENTS

| | | |
|---|---|---|
| 3,683,923 A | 8/1972 | Anderson |
| 4,712,558 A | 12/1987 | Kidd et al. ................... 128/421 |
| 4,940,453 A | 7/1990 | Cadwell ........................... 600/13 |
| 4,995,395 A | 2/1991 | Ilmoniemi et al. ............ 128/653 |
| 5,047,005 A | 9/1991 | Cadwell ........................... 600/13 |
| 5,061,234 A | 10/1991 | Chaney ............................ 600/14 |
| 5,097,833 A | 3/1992 | Campos |
| 5,116,304 A | 5/1992 | Cadwell ........................... 600/13 |
| 5,299,569 A | 4/1994 | Wernicke et al. |
| 5,655,534 A | 8/1997 | Ilmoniemi ................. 128/653.1 |
| 5,766,124 A | 6/1998 | Polson ............................. 600/13 |
| 5,769,778 A | 6/1998 | Abrams et al. .................. 600/14 |
| 5,813,970 A | 9/1998 | Abrams et al. .................. 600/14 |
| 5,871,517 A | 2/1999 | Abrams et al. .................. 607/45 |
| 5,969,505 A | 10/1999 | Okamura |
| 6,066,084 A | 5/2000 | Edrich et al. .................... 600/13 |
| 6,117,066 A | 9/2000 | Abrams et al. .................. 600/14 |
| 6,179,769 B1 | 1/2001 | Ishikawa et al. .................. 600/9 |
| 6,179,770 B1 | 1/2001 | Mould ............................. 600/13 |
| 6,179,771 B1 | 1/2001 | Mueller |
| 6,198,958 B1 | 3/2001 | Ives et al. ....................... 600/411 |
| 6,253,109 B1 | 6/2001 | Gielen ............................. 607/45 |
| 6,256,531 B1 | 7/2001 | Ilmoniemi et al. ............ 600/544 |
| 6,266,556 B1 | 7/2001 | Ives et al. ....................... 600/544 |
| 6,366,814 B1 | 4/2002 | Boveja et al. ................... 607/45 |
| 6,389,318 B1 | 5/2002 | Zarinetchi et al. |
| 6,434,410 B1 | 8/2002 | Cordero et al. ............... 600/396 |
| 6,463,328 B1 | 10/2002 | John ............................... 607/45 |
| 6,477,422 B1 | 11/2002 | Splett |

(Continued)

FOREIGN PATENT DOCUMENTS
EP 998 958 A3 5/2000
(Continued)

OTHER PUBLICATIONS

Hess, C.W. et al., "Magnetic Stimulation of the Human Brain: Influence of Size and Shape of the Stimulating Coil", *Motor Disturbances II*, Jun. 1988, 31-42.

(Continued)

*Primary Examiner* — John Lacyk
(74) *Attorney, Agent, or Firm* — Condo Roccia LLP

(57) ABSTRACT

The inventive technique includes methods, devices and computer-readable media for monitoring a magnetic device. One such device includes a magnetic core for generating a magnetic field, a power supply and a capacitor bank that is charged by the power supply and is for pulsing the magnetic core. The device also includes a processor that measures a charging response of the capacitor bank during charging and determines whether the measured charging response is within a predetermined tolerance of a predetermined charging response.

46 Claims, 6 Drawing Sheets

U.S. PATENT DOCUMENTS

| | | | |
|---|---|---|---|
| 6,480,743 B1 | 11/2002 | Kirkpatrick et al. | 607/45 |
| 6,484,059 B2 | 11/2002 | Gielen | |
| 6,488,617 B1 | 12/2002 | Katz | 600/26 |
| 6,497,648 B1 | 12/2002 | Rey | |
| 6,516,288 B2 | 2/2003 | Bagne | |
| 6,537,197 B1 | 3/2003 | Ruohonen et al. | 600/13 |
| 6,551,233 B2 | 4/2003 | Perreault et al. | 600/9 |
| 6,560,490 B2 | 5/2003 | Grill et al. | |
| 6,571,123 B2 | 5/2003 | Ives et al. | 600/544 |
| 6,572,528 B2 | 6/2003 | Rohan et al. | 600/14 |
| 6,591,138 B1 | 7/2003 | Fischell et al. | 607/45 |
| 6,629,935 B1 | 10/2003 | Miller et al. | 600/558 |
| 6,663,556 B2 | 12/2003 | Barker | 600/14 |
| 6,671,155 B2 | 12/2003 | Bennett et al. | 361/118 |
| 6,687,627 B1 | 2/2004 | Gunn et al. | |
| 6,827,681 B2 | 12/2004 | Tanner et al. | |
| 6,849,040 B2 | 2/2005 | Ruohonen et al. | 600/14 |
| 6,978,179 B1 | 12/2005 | Flagg et al. | 607/45 |
| 2001/0031906 A1 | 10/2001 | Ishikawa et al. | 600/13 |
| 2002/0087201 A1 | 7/2002 | Firlik et al. | 607/45 |
| 2002/0091419 A1 | 7/2002 | Firlik et al. | 607/45 |
| 2002/0103515 A1 | 8/2002 | Davey et al. | 607/66 |
| 2003/0023159 A1 | 1/2003 | Tanner | |
| 2003/0050527 A1 | 3/2003 | Fox et al. | 600/13 |
| 2003/0073899 A1 | 4/2003 | Ruohonen et al. | |
| 2003/0074032 A1 | 4/2003 | Gliner | 607/45 |
| 2003/0088274 A1 | 5/2003 | Gliner et al. | 607/3 |
| 2003/0097161 A1 | 5/2003 | Firlik et al. | 607/72 |
| 2003/0125786 A1 | 7/2003 | Gliner et al. | 607/116 |
| 2003/0130706 A1 | 7/2003 | Sheffield et al. | 607/46 |
| 2004/0001937 A1 | 1/2004 | Nissing et al. | 428/131 |
| 2004/0077921 A1 | 4/2004 | Becker et al. | 600/9 |
| 2004/0138578 A1 | 7/2004 | Pineda et al. | 600/544 |
| 2004/0153129 A1 | 8/2004 | Pless et al. | 607/62 |
| 2004/0251934 A1 | 12/2004 | Yano et al. | |
| 2005/0021104 A1 | 1/2005 | DiLorenzo | 607/45 |
| 2005/0182288 A1 | 8/2005 | Zabara | |
| 2005/0216071 A1 | 9/2005 | Devlin et al. | 607/48 |
| 2005/0228209 A1 | 10/2005 | Schneider et al. | 600/13 |
| 2005/0256539 A1 | 11/2005 | George et al. | |

FOREIGN PATENT DOCUMENTS

| | | |
|---|---|---|
| EP | 1 273 320 A1 | 1/2003 |
| WO | WO 99/55421 A2 | 11/1999 |
| WO | WO 99/64884 A1 | 12/1999 |
| WO | WO 01/28622 A2 | 4/2001 |
| WO | WO 01/97906 A2 | 12/2001 |
| WO | WO 02/32504 A2 | 4/2002 |
| WO | WO 02/072914 A2 | 9/2002 |
| WO | WO 02/085449 A2 | 10/2002 |
| WO | WO 02/085454 A1 | 10/2002 |
| WO | WO 02/089902 A2 | 11/2002 |
| WO | WO 02/094997 A2 | 11/2002 |
| WO | WO 03/035163 A2 | 5/2003 |
| WO | WO 2004/100765 A2 | 11/2004 |
| WO | WO 2005/000401 A1 | 1/2005 |
| WO | WO 2005/065768 A1 | 7/2005 |

OTHER PUBLICATIONS

Wassermann, E.M., "Repetitive Transcranial Magnetic Stimulation: An Introduction and Overview", *CNS Spectrums*, 7 pages, Jan. 1997.
International Patent Application No. PCT/US2008/002088: International Search Report dated Jul. 18, 2008, 4 page.
International Patent Application No. PCT/US2008/002088: Written Opinion dated Jul. 18, 2008, 8 pages.
International Patent Application No. PCT/US2008/002088: Notification of Transmittal of International Preliminary Report on Patentability dated Jun. 16, 2009, 5 pages.

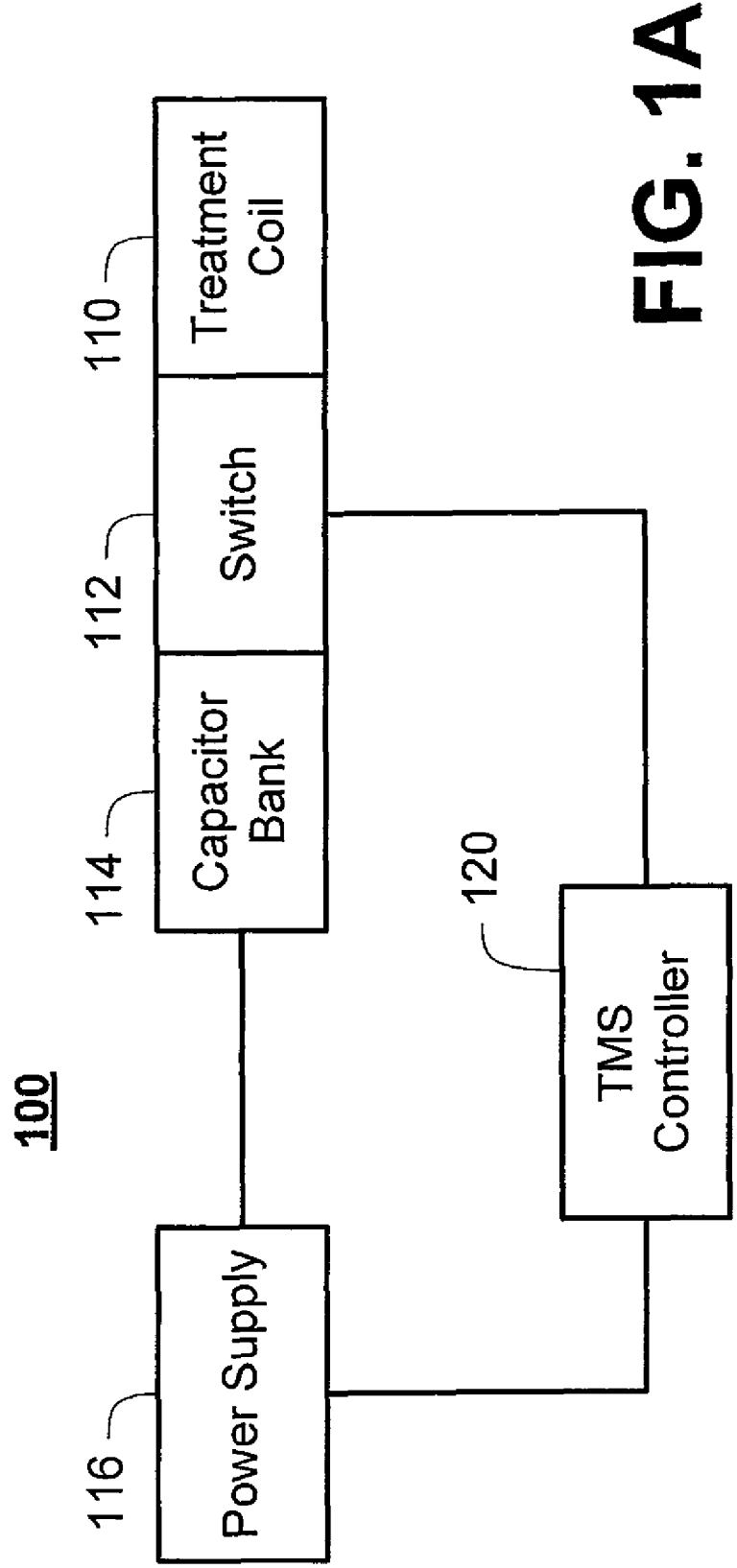

CAPACITOR FAILURE DETECTION

BACKGROUND

A number of medical ailments are treated and/or diagnosed through the application of a magnetic field to an afflicted portion of a patient's body. Neurons and muscle cells are a form of biological circuitry that carry electrical signals and respond to electromagnetic stimuli. When an ordinary conductive wire loop is passed through a magnetic field or is in the presence of a changing magnetic field, an electric current is induced in the wire.

The same principle holds true for conductive biological tissue. When a changing magnetic field is applied to a portion of the body, neurons may be depolarized and stimulated. Muscles associated with the stimulated neurons can contract as though the neurons were firing by normal causes.

A nerve cell or neuron can be stimulated in a number of ways, including transcutaneously via transcranial magnetic stimulation (TMS), for example. TMS uses a rapidly changing magnetic field to induce a current on a nerve cell, without having to cut or penetrate the skin. The nerve is said to "fire" when a membrane potential within the nerve rises with respect to its normal negative ambient level of approximately −90 mV, depending on the type of nerve and local pH of the surrounding tissue.

The use of magnetic stimulation is very effective in rehabilitating injured or paralyzed muscle groups. Apart from stimulation of large muscle groups such as the thigh or the abdomen, experimentation has been performed in cardiac stimulation as well. In this context, magnetic stimulation of the heart may prove to be superior to CPR or electrical stimulation, because both of those methods undesirably apply gross stimulation to the entire heart all at once.

Another area in which magnetic stimulation is proving effective is treatment of the spine. The spinal cord is difficult to access directly because vertebrae surround it. Magnetic stimulation may be used to block the transmission of pain via nerves in the back, e.g., those responsible for lower back pain.

Magnetic stimulation also has proven effective in stimulating regions of the brain, which is composed predominantly of neurological tissue. One area of particular interest is the treatment of depression. It is believed that more than 28 million people in the United States alone suffer from some type of neuropsychiatric disorder. These include conditions such as depression, schizophrenia, mania, obsessive-compulsive disorder, panic disorders, and others. Depression is the "common cold" of psychiatric disorders, believed to affect 19 million people in the United States and possibly 340 million people worldwide.

Modern medicine offers depression patients a number of treatment options, including several classes of anti-depressant medications (e.g., SSRI's, MAOI's and tricyclics), lithium, and electroconvulsive therapy (ECT). Yet many patients remain without satisfactory relief from the symptoms of depression. To date, ECT remains an effective therapy for resistant depression; however, many patients will not undergo the procedure because of its severe side effects.

Recently, repetitive transcranial magnetic stimulation (rTMS) has been shown to have significant anti-depressant effects for patients that do not respond to the traditional methods. The principle behind rTMS is to apply a subconvulsive stimulation to the prefrontal cortex in a repetitive manner, causing a depolarization of cortical neuron membranes. The membranes are depolarized by the induction of small electric fields in excess of 1 V/cm that are the result of a rapidly changing magnetic field applied non-invasively.

To produce the rapidly changing magnetic field needed to induce a current on a nerve cell in connection with any of the above treatments, a magnetic stimulation device typically includes one or more energy storage capacitors. The capacitors provide the magnetic stimulation device with the high power and quick re-charging time needed to repetitively pulse a magnetic field generator, such as a magnetic core, in a manner required by the desired treatment regimen. Because the capacitors in such an arrangement directly power the magnetic core that provides the magnetic pulses to a patient, any change in the capacitance directly changes the magnetic energy of the pulse delivered to the patient.

Thus, in a magnetic stimulation device that includes a single capacitor, if the single capacitor suffers a complete failure (e.g., open circuit condition), the failure can be easily detected—either because the magnetic core will not pulse, or because the generated pulse will be substantially different from the expected pulse. Conventional start-up diagnostic routines can typically detect this type of failure. Alternately, these failures may be obvious to the treatment provider. For example, readings from a sensor that detects the magnetic field pulse generated by the magnetic core (i.e., a "field sensor") may be used to determine that the generated magnetic pulse does not have one or more desired characteristics as a result of a capacitor failure.

In some situations, however, the performance of one or more capacitors may degrade slightly over time. For example, one or more capacitors may experience excessive parametric drift. In addition, more than one capacitor may be arranged in a multi-capacitor bank, in which the capacitors are typically connected in parallel. In such a situation, when a single capacitor fails (e.g., causes an open circuit) the overall capacitance of the bank may only decrease by a small percentage. In such situations, the generated pulse may vary from the desired pulse in subtle ways that conventional field sensors cannot detect because the field sensing equipment may have a wide pass/fail threshold to allow for component tolerances and sensor positional variation of the field sensor's position.

As a result, the magnetic device may appear to operate correctly, but actually may be producing magnetic pulses outside of published device specifications, potentially resulting in improper therapy being delivered to the patient. Delivering an incorrect magnetic pulse to a patient can affect the magnetic stimulation treatment adversely. For example, the treatment provider may believe that the patient is not responding to the treatment, when in fact the intended treatment is not being delivered to the patient. Thus, the treatment provider may be lead to make treatment decisions based on faulty information.

In addition, conventional mechanisms for determining whether the generated magnetic pulse is within tolerances have such a coarse level of magnetic field detection that "pass/fail" determinations are the only type of result that can be provided to a treatment provider. Thus, a treatment provider that is confronted with a magnetic stimulator failure does not know how far out of tolerance the magnetic device actually is, and either has to end the treatment or use a spare device, if one is available. Either course of action is usually inconvenient and potentially expensive.

SUMMARY

In view of the foregoing drawbacks and shortcomings, methods, devices and computer-readable media for monitoring a magnetic device are provided. One such device includes a magnetic core for generating a magnetic field, a power supply and a capacitor bank that is charged by the power supply and is for pulsing the magnetic core. The device also includes a processor that measures a charging response of the capacitor bank during charging and determines whether the measured charging response is within a predetermined tolerance of a predetermined charging response.

In one method, the charging of a capacitor bank that is adapted to pulse a magnetic core to generate a magnetic field in a magnetic device is detected. A charging response of the capacitor bank is measured during the charging and is compared to a predetermined charging response. A determination is made to determine whether the measured charging response is within a predetermined tolerance of the predetermined charging response.

BRIEF DESCRIPTION OF THE DRAWINGS

FIGS. 1A-B illustrate an example magnetic device in which aspects of an embodiment may be implemented;

DETAILED DESCRIPTION

Figure 1B:
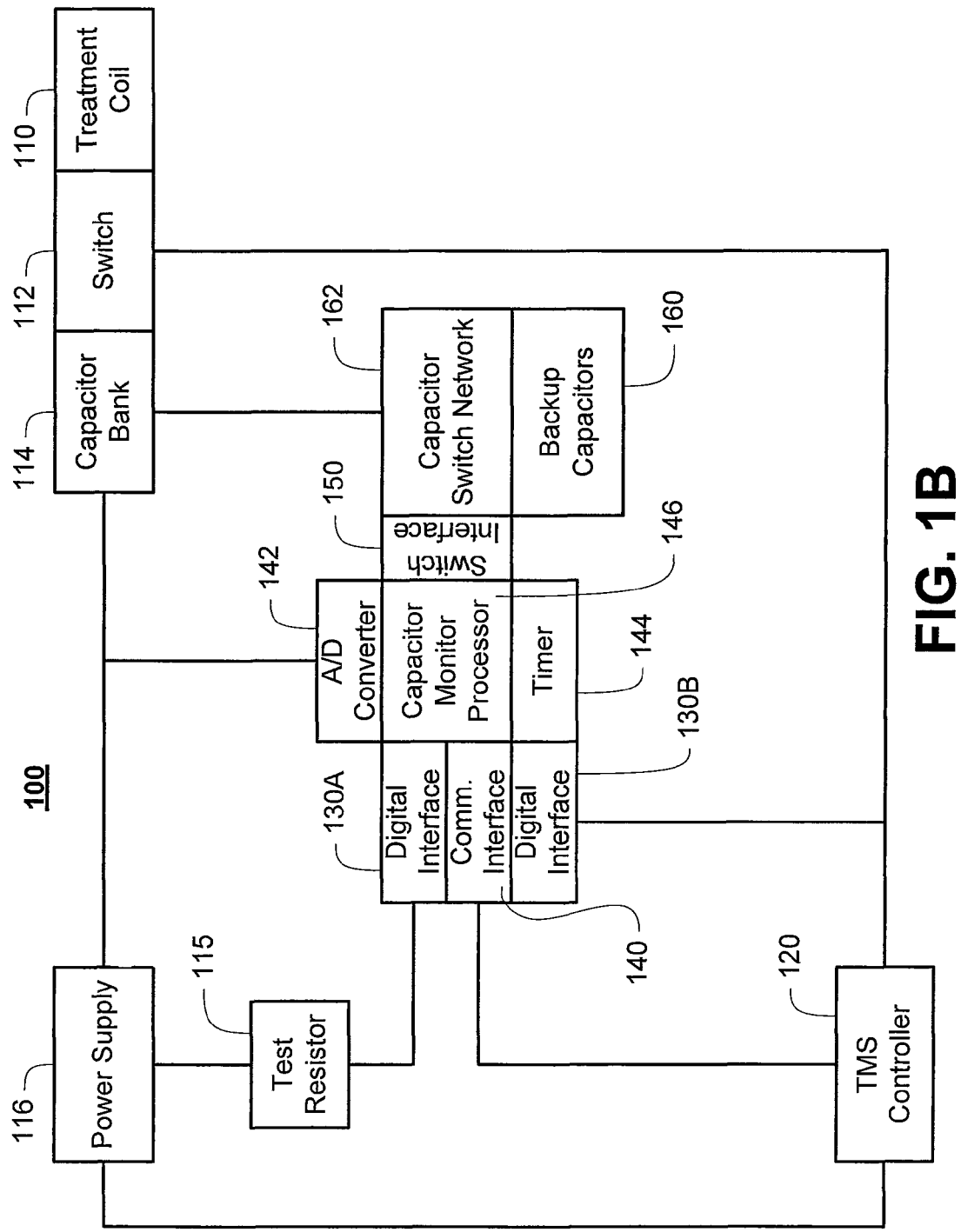

The subject matter of the disclosed embodiments is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Overview

In one embodiment, a feedback circuit is included at the output of a magnetic stimulation device's capacitor charging circuit. The feedback circuit provides information regarding the output to a controller circuit. The controller circuit measures a charging response (e.g., the dV/dt of the capacitors, a capacitance value derived therefrom, or the like) in the capacitor charge circuit during a charging period. Such measurements may take place over repeated charging periods, or may be based on a single measurement. In one alternative embodiment, the controller circuit measures a discharging response in the capacitor charge circuit during a discharging period. In another alternative embodiment, the controller circuit measures a response of a power supply during either charging or discharging of the capacitor charge circuit.

Once the measurement(s) are completed, the controller circuit compares the measurements to a standard value in a calibration table. The standard value may be based on an ideal capacitor or power supply response, or may be based on the actual capacitor's or power supply's response during a calibration process to account for normal capacitor or power supply tolerance variations.

If the measured charging or discharging response is not within a predetermined tolerance of the value in the calibration table, the magnetic stimulation device may notify a device operator. In addition, the magnetic stimulation device may provide an option to the operator such as, for example, an option to modify the device settings to compensate for the out-of-tolerance condition.

Magnetic Device Overview

For purposes of explanation and context, an overview of the operation and applications of a magnetic device in which aspects of the various embodiments may be implemented is now discussed. As is well known to those skilled in the art, the magnitude of an electric field induced on a conductor is proportional to the rate of change of magnetic flux density across the conductor. When an electric field is induced in a conductor, the electric field creates a corresponding current flow in the conductor. The current flow is in the same direction of the electric field vector at a given point. The peak electric field occurs when the time rate of change of the magnetic flux density is the greatest and diminishes at other times. During a magnetic pulse, the current flows in a direction that tends to preserve the magnetic field (i.e., Lenz's Law).

As may be appreciated, various devices may take advantage of the above principles to induce an electric field, and such devices may be used in a variety of applications. For example, magnetic devices may be used for electrical stimulation of the anatomy, and the like. While the discussion herein focuses on magnetic devices that are used in connection with magnetic stimulation of anatomical tissue, it will be appreciated that such discussion is so limited solely for purposes of explanation and clarity. Thus, it will be understood that an embodiment is equally applicable to any application of a magnetic device in any field of endeavor. Thus, the present discussion of magnetic devices should not be construed as limiting embodiments of the invention to medical or other applications.

Therefore, and turning now to the context of electrical stimulation of the anatomy, certain parts of the anatomy (e.g., nerves, tissue, muscle, brain) act as a conductor and carry electric current when an electric field is applied. The electric field may be applied to these parts of the anatomy transcutaneously by applying a time varying (e.g., pulsed) magnetic field to the portion of the body. For example, in the context of TMS, a time-varying magnetic field may be applied across the skull to create an electric field in the brain tissue, which produces a current. If the induced current is of sufficient density, neuron action potential may be reduced to the extent that the membrane sodium channels open and an action potential response is created. An impulse of current is then propagated along the axon membrane that transmits information to other neurons via modulation of neurotransmitters. Such magnetic stimulation has been shown to acutely affect glucose metabolism and local blood flow in cortical tissue. In the case of major depressive disorder, neurotransmitter dysregulation and abnormal glucose metabolism in the prefrontal cortex and the connected limbic structures may be a likely pathophysiology. Repeated application of magnetic stimulation to the prefrontal cortex may produce chronic changes in neurotransmitter concentrations and metabolism so that depression is alleviated.

In a similar fashion, non-cortical neurons (e.g., cranial nerves, peripheral nerves, sensory nerves) may also be stimulated by an induced electric field. Techniques have been developed to intentionally stimulate peripheral nerves to diagnose neuropathologies by observing response times and conduction velocities in response to a pulsed magnetic field induced stimulus. Discomfort and/or pain may result if the induced electric field applied to a peripheral or cranial nerve is very intense or focused on a small area of such a nerve. This discomfort may be diminished by intentionally over-stimulating the sensory nerves in the affected nerve bundle so that they can no longer respond to external pain stimuli, or by reducing the intensity and focus of the induced electric field that is causing the pain sensation.

As noted above, it should be appreciated that transcutaneous magnetic stimulation is not limited to treatment of depression. In addition to depression, the transcutaneous magnetic stimulation methods and apparatus of the invention may be used to treat a patient such as a human suffering from epilepsy, schizophrenia, Parkinson's disease, Tourette's syndrome, amyotrophic lateral sclerosis (ALS), multiple sclerosis (MS), Alzheimer's disease, attention deficit/hyperactivity disorder, obesity, bipolar disorder/mania, anxiety disorders (e.g., panic disorder with and without agoraphobia, social phobia also known as social anxiety disorder, acute stress disorder and generalized anxiety disorder), post-traumatic stress disorder (one of the anxiety disorders in DSM), obsessive compulsive disorder (also one of the anxiety disorders in DSM), pain (such as, for example, migraine and trigeminal neuralgia, as well as chronic pain disorders, including neuropathic pain, e.g., pain due to diabetic neuropathy, post-herpetic neuralgia, and idiopathic pain disorders, e.g., fibromyalgia, regional myofascial pain syndromes), rehabilitation following stroke (neuro plasticity induction), tinnitus, stimulation of implanted neurons to facilitate integration, substance-related disorders (e.g., dependence, abuse and withdrawal diagnoses for alcohol, cocaine, amphetamine, caffeine, nicotine, cannabis and the like), spinal cord injury and regeneration/rehabilitation, stroke, head injury, sleep deprivation reversal, primary sleep disorders (primary insomnia, primary hypersomnia, circadian rhythm sleep disorder), cognitive enhancements, dementias, premenstrual dysphoric disorder (PMS), drug delivery systems (changing the cell membrane permeability to a drug), induction of protein synthesis (induction of transcription and translation), stuttering, aphasia, dysphagia, essential tremor, and/or eating disorders (such as bulimia, anorexia and binge eating).

Example Magnetic Stimulation Device

A ferromagnetic core may be used in connection with a magnetic device to produce a magnetic field. In some embodiments, such a magnetic field may be for purposes of carrying out transcutaneous magnetic stimulation such as, for example, Transcranial Magnetic Stimulation (TMS), Repetitive TMS (rTMS), Magnetic Seizure Therapy (MST), reduction of peripheral nerve discomfort and so forth. Again, although some of the examples that follow may be discussed in connection with TMS and rTMS embodiments for the purposes of explanation and clarity, any type of transcutaneous magnetic stimulation, including all of those listed above, may be performed according to an embodiment of the invention. In addition, and as noted above, embodiments of the invention are not limited to transcutaneous magnetic stimulation, as an embodiment may be used in connection with magnetic devices that generate a magnetic field for any purpose.

Furthermore, the embodiments presented herein are not limited to the use of ferromagnetic core magnetic stimulation devices, as other core materials may be used such as, for example, air. The discussion herein therefore describes a ferromagnetic core magnetic stimulation device solely for purposes of explanation and clarity. In an embodiment, a ferromagnetic core may be approximately hemispherical, and in another embodiment the ferromagnetic core may include a highly saturable magnetic material having a magnetic saturation of at least 0.5 Tesla. In some embodiments, a ferromagnetic core may be shaped to optimize the magnetic field distribution in the treatment area. Treatment areas for other forms of treatment (e.g., reduction of discomfort in peripheral nerves, etc.) may be more or less deep than is the case for TMS.

FIGS. 1A-B are diagrams illustrating an example magnetic device 100. In magnetic device 100, power supply 116, capacitor bank 114, switch 112 and TMS controller 120 form an electric circuit that provides a power signal to treatment coil 110. The power signal may be any time-varying electric signal capable of generating an electric and/or magnetic field. The treatment coil 110 may be used to conduct transcranial magnetic stimulation (TMS) and/or repetitive transcranial magnetic stimulation (rTMS).

Power supply 116 may be any type of power source that provides sufficient energy for treatment coil 110 to generate a magnetic field for its intended purpose—whether for TMS, rTMS, MST or any other type of application. For example, power supply 116 may be a conventional 120 or 240 VAC main power source. Capacitor bank 114 provides energy storage for pulsing treatment coil 110. While referred to herein as a "bank" of capacitors, capacitor bank 114 may, in some embodiments, be comprised of a single capacitor. Thus, it should be appreciated that the references herein to a "bank" of capacitors does not require more than one capacitor to be present in said bank 114.

Capacitor bank 114 may be used, for example, in applications where only a 120 VAC power source or the like is available. A typical doctor's office may only be equipped with a conventional (e.g., 120 VAC or the like) power supply rather than a higher-power 240 VAC or three-phase power supply. Capacitor bank 114 can be used to produce higher peak currents in treatment coil 110 than would be possible by driving the treatment coil directly from power supply 116 alone. For example, power supply 116 may convert 120 VAC at its input to 1500 VDC at its output, with the DC output capable of producing 1 Amp DC at 1500 VDC. In an embodiment, adding capacitor 114 allows much higher peak pulse current to flow into treatment coil 116 than the 1 Amp produced by power supply 116. In such an embodiment, capacitor 114 can be charged up to power supply 116's output voltage in the time period between pulses that are delivered to treatment coil 110. When switch 112 activates to produce the pulse in treatment coil 110, peak currents in excess of 1000 A can be delivered to treatment coil 110 from the charge stored on capacitor 114. The magnitude of this peak current may be dictated primarily by the inductance of treatment coil 110, and by the capacitance value and voltage level stored on capacitor 114 prior to the pulse. It will be appreciated that capacitor bank 114 may be used regardless of the type of power supply 116 available. For example, capacitor bank 114 may be used in situations where power supply 116 is a 240 VAC or three-phase power supply to, for example, produce desired peak currents for input into treatment coil 110.

Capacitor bank 114 may include any number and/or type of capacitor(s) that are appropriate for the power level, charging time and/or pulse type required by device 100. For example, in one non-limiting embodiment, eight 10 μF capacitors may be connected in parallel to result in 80 μF of total capacitance. As noted above, a single 80 μF capacitor, for example, could be used in connection with an embodiment.

Switch 112 may be any type of electrical switching device that can operate treatment coil 110 by switching power from capacitor bank 114 and/or power supply 116 on and off. For example, switch 112 may be operated to switch power from power supply 116 to charge capacitor bank 114. Switch may also be used to discharge capacitor bank 114 through treatment coil 110, thereby creating a magnetic field that can be used for TMS treatment, for example. TMS controller 120 may be any type of hardware, software, or combination thereof, that controls switch 112 and/or power supply 116.

FIG. 1B is a diagram that also illustrates device 100 with greater detail than FIG. 1A to more fully explain an embodiment. It will be appreciated that embodiments are not limited to a device 100 as depicted in FIG. 1A or 1B, and other configurations of components are consistent with such embodiments.

Power supply 116, capacitor bank 114, switch 112, TMS controller 120 and treatment coil 110 are as discussed above in connection with FIG. 1A. While a feedback circuit component is illustrated in FIG. 1B as being comprised of digital interfaces 130A-B, communication interface 140, A/D converter 142, timer 144, capacitor monitor processor 146, switch interface 150, capacitor switch network 162 and backup capacitor bank 160, in an embodiment any or all of these components may be integrated into a single magnetic device. Thus, it should be appreciated that these components are illustrated as separate for purposes of discussion and embodiments of the invention—as well as various configurations of a feedback circuit used therein—are not limited to the configuration depicted in FIG. 1B. Furthermore, various embodiments contemplate that more or fewer components than are depicted in FIG. 1B may be present in device 100, and therefore the presence of any of these components in FIG. 1B does not limit embodiments to the depicted configuration. In addition, any or all of digital interfaces 130A-B, communication interface 140, A/D converter 142, timer 144, capacitor monitor processor 146, switch interface 150, capacitor switch network 162 and backup capacitor bank 160 may be implemented as any combination of hardware and/or software. For example, and of the above components may be implemented as computer-readable instructions stored on a computer-readable medium (e.g., CD-ROM, DVD, encoded signal, etc.).

Digital interfaces 130A-B are provided to interface with power supply 116 and TMS controller 120, respectively. It will be appreciated that both power supply 116 and TMS controller 120, in one embodiment, may be capable of digital communication and therefore may be connected with digital interfaces 130A-B to enable communication with other components of device 100. In another embodiment, one or both of power supply 116 and TMS controller 120 may be capable only of analog communications, in which case an analog to digital (A/D) converter may be needed to enable such communications with other components of device 100. For example, an attenuated representation of the capacitor voltage may be fed into A/D converter 142. Communication interface 140 enables communication between power supply 116, TMS controller 120 and capacitor monitor processor 146. In addition, communication interface 140 may permit communication between device 100 and a manufacturer, maintenance facility, or the like. In such an embodiment, communication interface 140 itself, or components available to communication interface 140, may be adapted to communicate over any type of communication channel such as, for example, a telephone line, the Internet (by way of a cable modem, T1 connection, digital subscriber line or the like), an intranet, and so forth. In another embodiment, communication interface 140 may be a RS232—compliant interface or the like.

Capacitor monitor processor 146 monitors the condition (in terms of, for example, charging response) of capacitor bank 114. In one embodiment capacitor monitor processor 146 may be a microcontroller, such as a Microchip PIC or Freescale 68HC08 family controller. In one embodiment, capacitor monitor processor 146—or a memory that is in operative communications with capacitor monitor processor 146—may store information relating to capacitor bank 114. For example, such memory (not shown in FIG. 1B for clarity) may include operating specifications such as the permissible dV/dt response for the capacitor bank when being charged. Such information may be used as will be discussed below in connection with FIGS. 2 and 3. Capacitor monitor processor 146 may use A/D converter 142 to monitor capacitor bank 114 during charging and discharging, as will be discussed below in connection with FIGS. 2 and 3. In connection with such monitoring, capacitor monitor processor 146 may use timer 144 to measure a predetermined portion of a charging time of capacitor bank 114 to provide capacitor monitor processor 146 with timing measurement capabilities.

Switch interface 150, capacitor switch network 162 and backup capacitor bank 160 may be used in an embodiment where one or more backup capacitor banks 160 are available in the event that capacitor bank 114 is no longer operating within specifications. Thus, switch interface 150 may serve to switch between capacitor bank 114 and one or more backup capacitor banks 160 by way of capacitor switch network 162.

FIG. 1B also includes resistor 115, which may be any component that acts as a resistor, and as a result resistor 115 may include one or more resistors and/or other components. Resistor 115 may serve to discharge capacitor bank 114 in connection with an embodiment to be discussed below in FIG. 4. Resistor 115 may have a primary purpose of discharging capacitor bank 114 during a test, or may have one or more other functions. Resistor 115 may include, or may be controlled by, a switching component that may, in one embodiment, cause resistor 115 to be electrically disconnected from one or more components of magnetic device 100 when resistor 115 is not in use.

Figure 2:
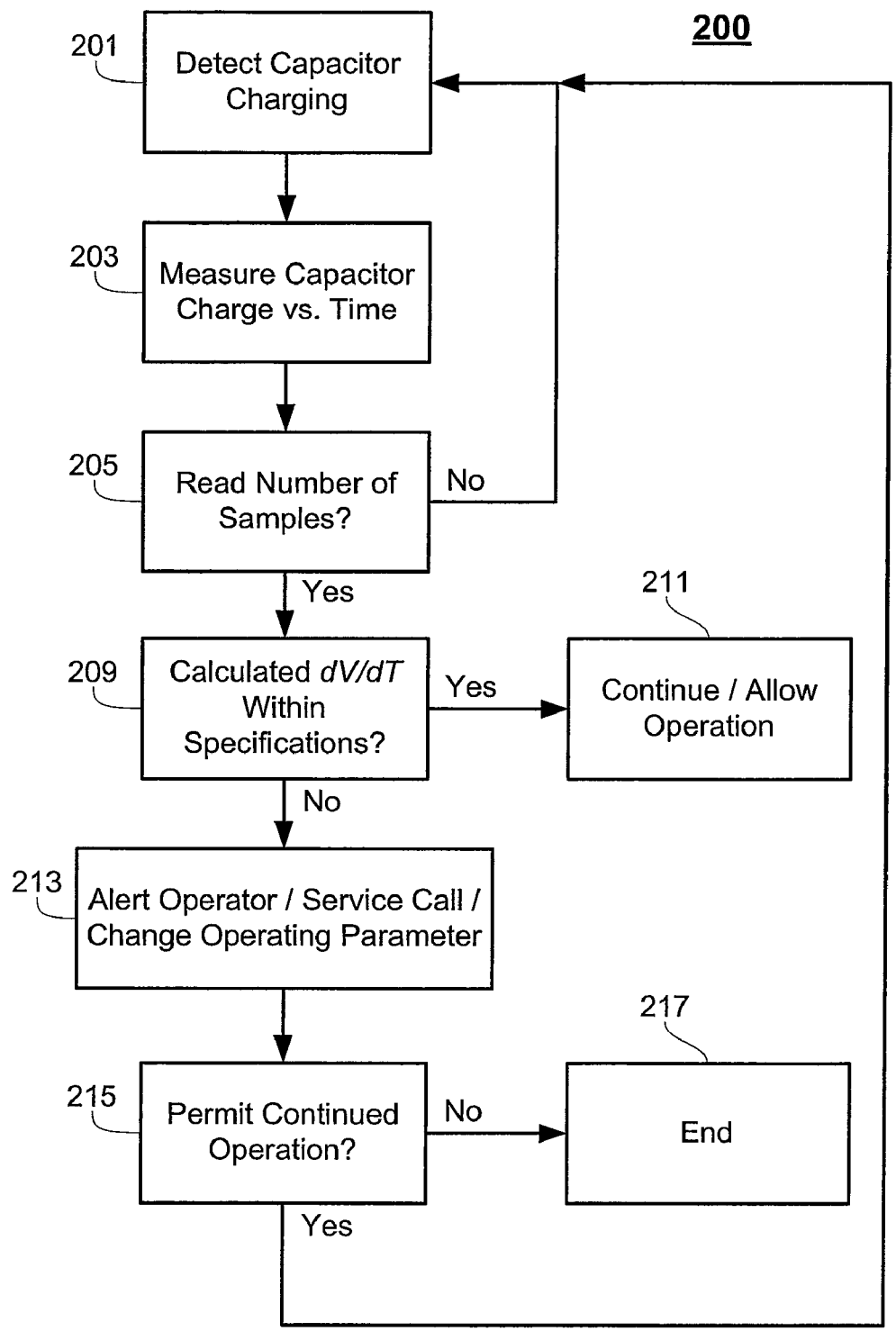
FIG. 2 is a flowchart illustrating an example method of testing one or more capacitors according to an embodiment.
Figure 3:
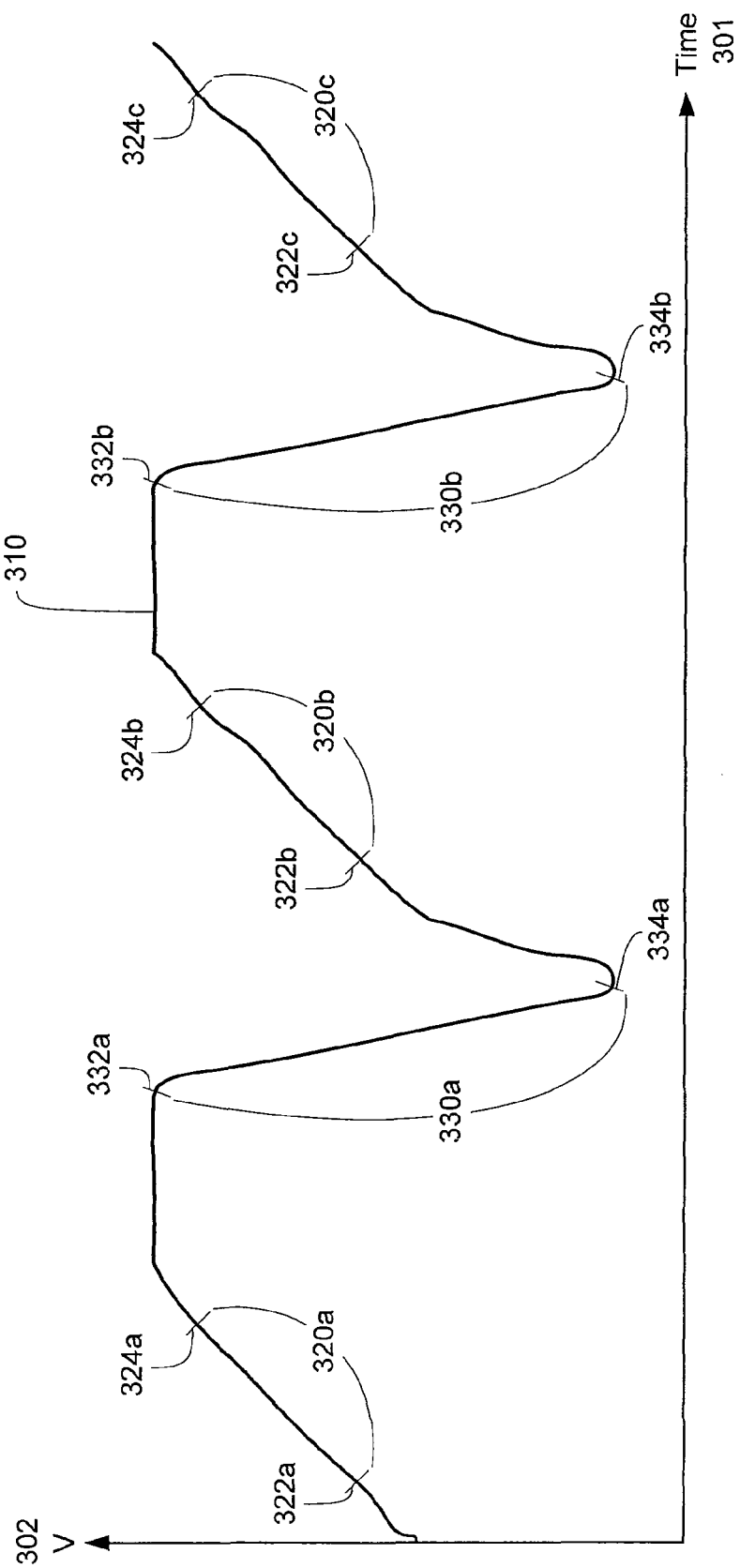
FIG. 3 is a plot of an example capacitor charging response according to an embodiment.

In the discussion that follows, references are made to FIGS. 2 and 3 as appropriate. FIG. 2 is a flowchart illustrating an example method 200 according to an embodiment, and FIG. 3 is an example plot 310 of the stored charge within a capacitor bank. As noted above, a capacitor bank may include one or more capacitors. Thus, plot 310 represents the stored charge of a capacitor bank in a magnetic device during three charging and two discharging periods. The stored charge is illustrated as Voltage on the Y-axis 302 and time is represented on the X-axis 301.

Segment 320a, which is a portion of plot 310 between start point 322a and end point 324a, represents a section of the charging response of the capacitor bank. A segment 320a may be selected so as to capture a substantially linear portion of plot 310 to enable a determination of the capacitor bank's dV/dt to be relatively straightforward. It will be appreciated that other sections of plot 310 within a charging period may be chosen, but if the sections are not substantially linear the calculation of the capacitor bank's dV/dt may become more complex. Thus, segment 320a may include a period of time that is less than the capacitor bank charging time.

To illustrate a series of charging and discharging periods, segments 320b-c and 330a-b are also shown in FIG. 3. Segments 320b-c illustrate sections of the charging response of the capacitor bank. Segment 320b is a portion of plot 310 located between start point 322*b* and end point 324*b*, and segment 320*c* is a portion of plot 310 located between start point 322*c* and end point 324*c*. Capacitor discharge is illustrated as segments 330*a-b*. Segment 330*a* is a portion of plot 310 between start point 332*a* and end point 334*a*. Likewise, segment 330*b* is a portion of plot 310 between start point 332*b* and end point 334*b*.

In one embodiment, method 200 may take place prior to the actual operation of the magnetic device such as, for example, part of a start-up routine. In another embodiment, method 200 may take place during operation or as part of a shut down routine. For example, in an embodiment in which method 200 is employed in connection with a TMS device, method 200 may take place during a start-up routine, and then may continue to take place during treatment to make sure the TMS device remains within specifications.

At step 201, a capacitor charging cycle (e.g., one of segments 320*a-c*) is detected. Such detection may occur by way of, for example, a determination that the stored charge in the capacitor bank (illustrated in FIG. 3 as plot 310) is increasing at a predetermined rate (e.g., the dV/dt of the capacitor bank is detected to reach a predetermined value, or the like). Alternatively, a timer, such as timer 144 as was discussed above in connection with FIG. 1B, may be used to select segment 320*a-c* of plot 310. For example, such a timer could be triggered by a predetermined voltage drop, such as the voltage drop illustrated as segment 330*a-b*, and could be set for a predetermined period of time to select segment 320*a-c* of plot 310.

At step 203, the capacitor charge, as a function of time, is measured. In one embodiment, the dV/dt of the capacitor bank is measured for one or more of segments 320*a-c*. It will be appreciated that in one embodiment each of segments 320*a-c* are selected so as to represent consistent portions of each charging curve. At step 205, a determination is made as to whether a predetermined number of samples has been read. For example, in one embodiment a single segment 320*a* may be measured, while in another embodiment multiple segments 320*a-c* may be measured and averaged. Multiple samples may be used to, for example, eliminate noise and other intermittent phenomena.

At step 209, a determination is made as to whether the calculated capacitance is within predetermined specifications/tolerances. Such a determination may be made by comparing the measured dV/dt to a predetermined dV/dt stored in a calibration table that is stored in device memory. For example, a calibration table can be generated during device manufacturing to facilitate the precise determination of failures during operation. This calibration table can be generated by measuring capacitor bank charge times at one or more charging voltages during production. These measurements can be used to adjust the pass/fail limits to account for normal manufacturing tolerances, such as the energy storage capacitance purchase tolerance, and the purchase tolerance of the charging power supply's output capacity. Alternatively, a capacitance of the capacitor bank may be calculated (using, for example, the measured dV/dt and knowledge of the output characteristics of the power supply used to charge the capacitor bank). This calculated capacitance may then be compared to a calibration table containing normal operating capacitances, for example.

If the determination of step 209 is that the calculated dV/dt is within predetermined specifications/tolerances, method 200 proceeds to step 211, where operation of the magnetic device is continued (if method 200 is being performed during operation) or allowed (if method 200 is being performed as part of a start-up, self-test or calibration sequence), for example.

If the determination of step 209 is that the calculated dV/dt is not within predetermined specifications/tolerances, method 200 proceeds to step 213, where an operator of the magnetic device may be notified of the out of tolerance condition. If appropriate, other information may be displayed and/or options presented on a display (not shown in FIG. 2 for clarity). Such a display may, in one embodiment, be conventional. For example, options for modifying the magnetic device's settings may be presented. Such options may permit some level of compensation for the out of tolerance condition of the capacitor bank such as, for example, to increase voltage, change the characteristics of the power signal from the power supply, etc. In another embodiment, a spare capacitor bank may be available and therefore an option or instructions may be presented to the operator with respect to switching to the spare capacitor bank. Step 213 may also (or alternatively) involve a service call. Such a service call may be made automatically via a telephone line or other electronic communication path (e.g., an email message by way of an Internet connection, etc.). In such a manner, a prompt service call may be arranged to repair or replace the magnetic device.

At step 215, a determination may be made as to whether continued operation can be permitted. For example, if a modification has been made to the magnetic device's settings, the determination of step 215 may involve testing the capacitor bank, the generated magnetic field, or one or more other parameters, to determine if the modification has sufficiently addressed the out of tolerance condition. If so, method 200 may either end or may repeat at step 201, where the testing begins again. If the determination of step 215 is that continued operation cannot be permitted, the magnetic device may discontinue operation, and may also alert the operator that continued operation is not permitted. For example, the magnetic device may determine that no amount of compensation will enable the generation of an acceptable magnetic field, and therefore the magnetic device should cease treatment operations.

Figure 4:
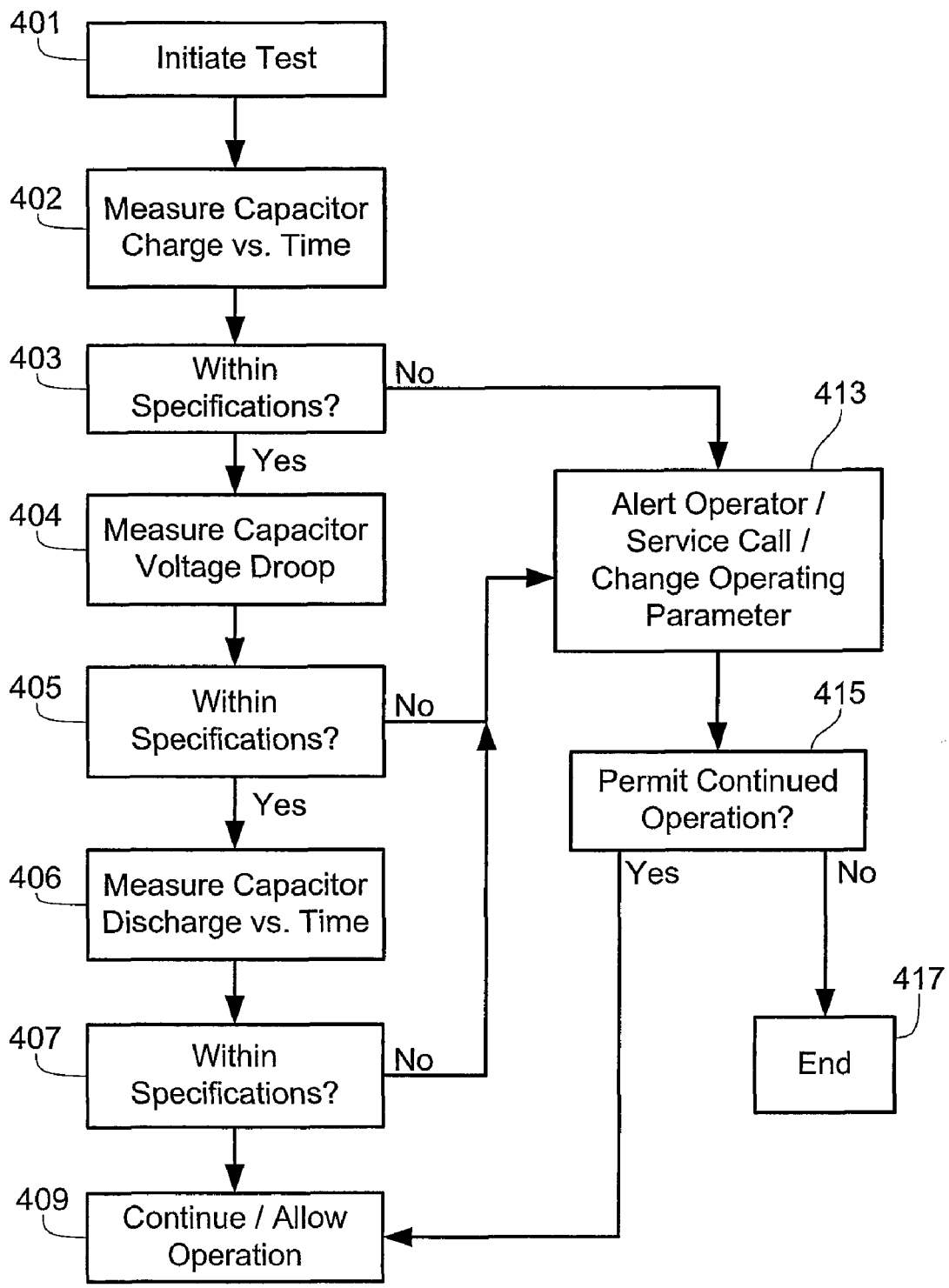
FIG. 4 is a flowchart illustrating an alternative example method of testing one or more capacitors according to an embodiment.
Figure 5:
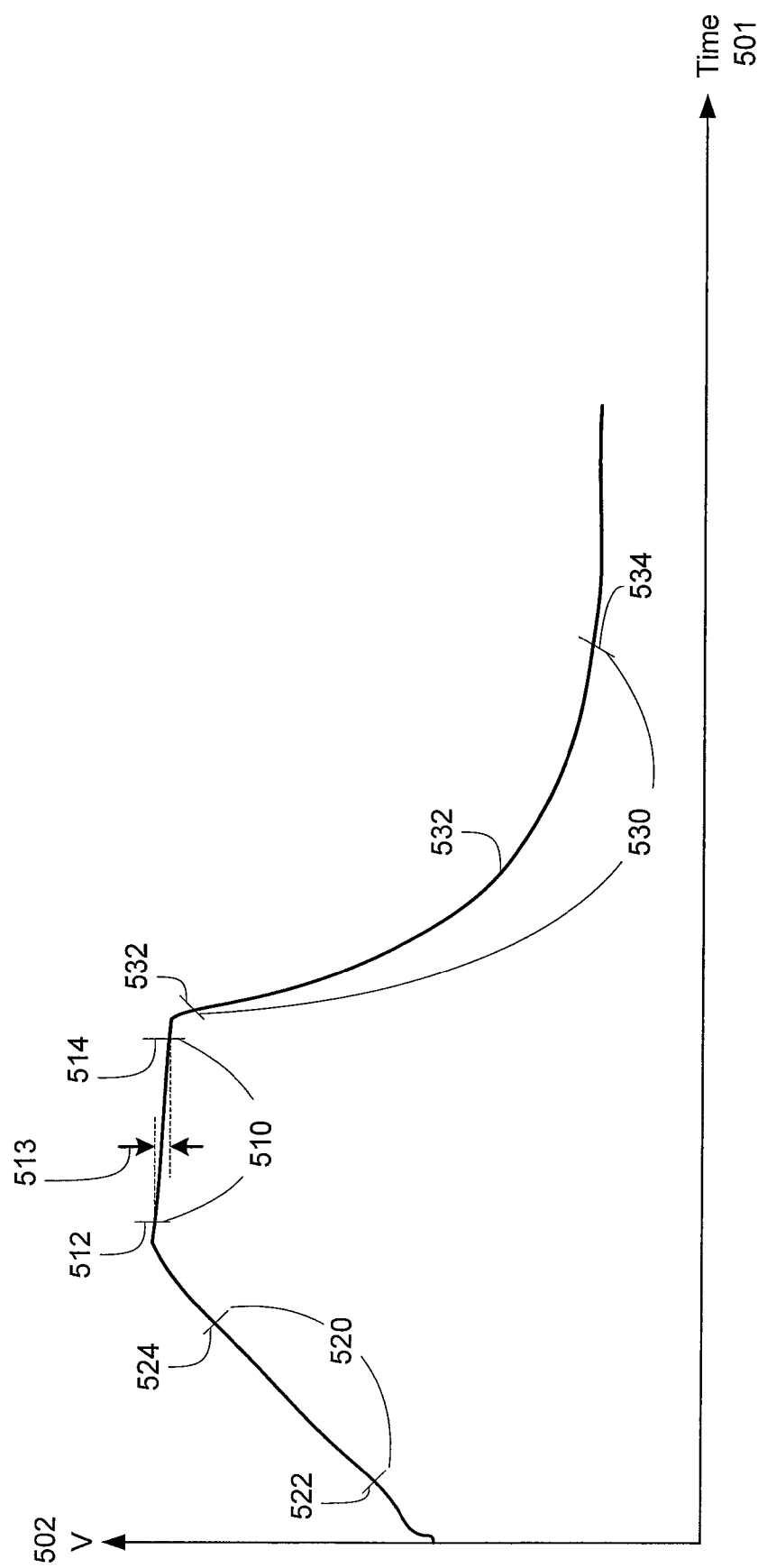
FIG. 5 is a plot of an example capacitor discharging response according to an embodiment.

In the discussion that follows, references are made to FIGS. 4 and 5 as appropriate. FIG. 4 is a flowchart illustrating an example method 400 according to an embodiment, and FIG. 5 is an example plot 500 of the stored charge within a capacitor bank. As noted above, a capacitor bank may include one or more capacitors. Thus, plot 500 represents the stored charge of a capacitor bank in a magnetic device during a single charging period 520, intermediate inactive period 510 and a discharging period 530. The stored charge is illustrated as Voltage on the Y-axis 502 and time is represented on the X-axis 501.

Segment 520, which is a portion of plot 500 between start point 522 and end point 524, represents a section of the charging response of the capacitor bank. Segment 520 may be selected so as to capture a substantially linear portion of plot 500 to enable a determination of the capacitor bank's dV/dt to be relatively straightforward. It will be appreciated that other sections of plot 500 within a charging period may be chosen, but if the sections are not substantially linear the calculation of the capacitor bank's dV/dt may become more complex. Thus, segment 520 may include a period of time that is less than the capacitor bank charging time.

Segment 510, which is a portion of plot 500 between start point 512 and end point 514, represents a section of the inactive response of the capacitor bank. During the inactive period represented by segment 510, the voltage level of the capacitor bank may "droop," or slowly decline over time, as represented by voltage droop 513. Such a droop may occur because of a flaw or degradation of the capacitor bank (or of a capacitor within the capacitor bank), or because of other factors. Capacitor discharge is illustrated as segment 530. Segment 530 is a portion of plot 500 between start point 532 and end point 534. The discharge represented by segment 530 may take place through, for example, test resistor 115 as discussed above in connection with FIG. 1B. Alternatively, the discharge may take place through treatment coil 110 or the like.

In one embodiment, method 400 may take place prior to the actual operation of the magnetic device such as, for example, part of a start-up routine. In another embodiment, method 400 may take place during operation or as part of a shut down routine. For example, in an embodiment in which method 400 is employed in connection with a TMS device, method 400 may take place during a start-up routine, and then may continue to take place during treatment to make sure the TMS device remains within specifications.

At step 401, a testing procedure is initiated. At step 402, the capacitor charge, as a function of time, is measured. In one embodiment, the dV/dt of the capacitor bank is measured for segment 520. At step 403, a determination is made as to whether the calculated capacitance is within predetermined specifications/tolerances. Such a determination may be made in a similar or different manner as was described above in connection with FIG. 2, for example.

If the determination of step 403 is that the calculated dV/dt is within predetermined specifications/tolerances, method 400 proceeds to step 404, where the voltage droop (represented by voltage droop 513 in FIG. 5) is measured. If the determination of step 403 is that the calculated dV/dt is not within predetermined specifications/tolerances, method 400 proceeds to step 413, where an operator of the magnetic device may be notified of the out of tolerance condition. If appropriate, other information may be displayed and/or options presented on a display (not shown in FIG. 4 for clarity). Such a display may, in one embodiment, be conventional. For example, options for modifying the magnetic device's settings may be presented. Such options may permit some level of compensation for the out of tolerance condition of the capacitor bank such as, for example, to increase voltage, change the characteristics of the power signal from the power supply, etc. In another embodiment, a spare capacitor bank may be available and therefore an option or instructions may be presented to the operator with respect to switching to the spare capacitor bank. Step 413 may also (or alternatively) involve a service call. Such a service call may be made automatically via a telephone line or other electronic communication path (e.g., an email message by way of an Internet connection, etc.). In such a manner, a prompt service call may be arranged to repair or replace the magnetic device.

Step 413 may be followed by step 415, a determination may be made as to whether continued operation can be permitted. For example, if a modification has been made to the magnetic device's settings, the determination of step 415 may involve testing the capacitor bank, the generated magnetic field, or one or more other parameters, to determine if the modification has sufficiently addressed the out of tolerance condition. If so, method 400 may either end or may repeat at step 401, where the testing begins again. In one embodiment, step 415 may take place once all of the measurements (as performed at step 402, as well as steps 404 and 406, which will be discussed below) are taken, and may determine whether operation may be permitted based on all of the measurements. In any event, if the determination of step 415 is that continued operation cannot be permitted, the magnetic device may discontinue operation, and may also alert the operator that continued operation is not permitted. For example, the magnetic device may determine that no amount of compensation will enable the generation of an acceptable magnetic field, and therefore the magnetic device should cease treatment operations.

As noted above, if the determination of step 403 is that the calculated dV/dt is within predetermined specifications/tolerances, method 400 proceeds to step 404, where the voltage droop (represented by voltage droop 513 in FIG. 5) is measured. In one embodiment, the voltage droop of the capacitor bank is measured for segment 510. At step 405, a determination is made as to whether the voltage droop is within predetermined specifications/tolerances. If the determination of step 405 is that the measured voltage droop is not within predetermined specifications/tolerances, method 400 proceeds to step 413. If the determination of step 405 is that the measured voltage droop is within predetermined specifications/tolerances, method 400 proceeds to step 406.

At step 406, the capacitor bank discharge, as a function of time, is measured. In one embodiment, the dV/dt of the capacitor bank is measured for segment 530. Any number of steps may take place in connection with step 406. For example, the capacitor bank may be electrically connected to a test resistor (such as test resistor 115 of FIG. 1B) and discharged for testing purposes or, in an alternative embodiment, the capacitor bank may be discharged for treatment purposes (i.e., through treatment coil 110 of FIG. 1B). In yet another embodiment, the capacitor bank may be discharged through treatment coil 110 for testing purposes (i.e., during a test pulse or the like).

At step 407, a determination is made as to whether the calculated capacitance is within predetermined specifications/tolerances. Such a determination may be made in a similar or different manner as was described above in connection with FIG. 2, for example.

If the determination of step 403 is that the calculated dV/dt is not within predetermined specifications/tolerances, method 400 proceeds to step 413 as was discussed above. If the determination of step 407 is that the calculated dV/dt is within predetermined specifications/tolerances, method 400 proceeds to step 409. At step 409 the operation of the magnetic device is continued (if method 400 is being performed during operation) or allowed (if method 400 is being performed as part of a start-up, self-test or calibration sequence), for example. While method 400 has been discussed above as measure each of a capacitor bank charging, inactive and discharging periods, it will be appreciated that an embodiment includes methods whereby any one or more of the measurements may be taken. For example, in one embodiment measurements for only the inactive and discharging periods may be used. Thus, it can be seen that an embodiment may include methods that measure the performance of a capacitor bank in any number of ways.

It is to be understood that the foregoing illustrative embodiments have been provided merely for the purpose of explanation and are in no way to be construed as limiting of the invention. Words used herein are words of description and illustration, rather than words of limitation. In addition, the advantages and objectives described herein may not be realized by each and every embodiment practicing the present invention. Further, although the invention has been described herein with reference to particular structure, materials and/or embodiments, the invention is not intended to be limited to the particulars disclosed herein. Rather, the invention extends to all functionally equivalent structures, methods and uses, such as are within the scope of the appended claims.

For example, although the disclosure addresses the treatment of patients, it should be appreciated that techniques described herein also contemplate patient diagnosis. In fact, where the disclosure refers to the treatment of patients for certain conditions, the techniques equally apply to the monitoring and diagnosis of patients for the same or similar conditions.

Those skilled in the art, having the benefit of the teachings of this specification, may affect numerous modifications thereto and changes may be made without departing from the scope and spirit of the invention.

What is claimed is:

1. A method for monitoring a magnetic device, the method comprising:
   detecting a charging of a capacitor bank in a magnetic device, wherein the capacitor bank is adapted to pulse a magnetic core to generate a magnetic field;
   measuring a charging response of the capacitor bank during said detected charging;
   comparing the measured charging response to a predetermined charging response;
   determining whether the measured charging response is within a predetermined tolerance of the predetermined charging response; and
   in response to whether the measured charging response is within a predetermined tolerance of the predetermined charging response, starting, modifying, continuing, or stopping operation of the magnetic device.

2. The method of claim 1, further comprising:
   measuring a discharging response of the capacitor bank during a discharging period;
   comparing the measured discharging response to a predetermined discharging response; and
   determining whether the measured discharging response is within a predetermined tolerance of the predetermined discharging response.

3. The method of claim 2, further comprising discharging the capacitor bank through one of a test capacitor and the magnetic core.

4. The method of claim 1, further comprising:
   measuring a voltage droop of the capacitor bank during an inactive period;
   comparing the measured voltage droop to a predetermined voltage droop; and
   determining whether the measured voltage droop is within a predetermined tolerance of the predetermined voltage droop.

5. The method of claim 1, further comprising providing an alert to a user if said determination is that the measured charging response is not within the predetermined tolerance of the predetermined charging response.

6. The method of claim 2, wherein providing said alert comprises providing an option to modify a power characteristic such that the magnetic field generated by the magnetic core is substantially equivalent to a desired magnetic field.

7. The method of claim 6, wherein the option is to increase a power input to the capacitor bank.

8. The method of claim 7, wherein the increase in power is proportional to a difference between the measured charging response and the predetermined charging response.

9. The method of claim 2, further comprising sending a message indicating that the measured charging response of the capacitor bank is out of the predetermined tolerance of the predetermined charging response.

10. The method of claim 9, wherein the message includes an identification of the magnetic device and an indication of the charging response of the capacitor bank.

11. The method of claim 9, wherein the message is an email message.

12. The method of claim 1, further comprising preventing the capacitor bank from pulsing the magnetic circuit if said determination is that the measured charging response is not within the predetermined tolerance of the predetermined charging response.

13. The method of claim 1, further comprising, if the measured charging response is not within the predetermined tolerance of the predetermined charging response, determining an adjustment to make to the operation of the capacitor bank to pulse the magnetic core to generate a magnetic pulse having a desired characteristic.

14. The method of claim 13, wherein the adjustment is increasing a charging voltage during charging of the capacitor bank.

15. The method of claim 1, further comprising permitting the capacitor bank to pulse the magnetic core if said determination is that the measured charging response is within the predetermined threshold of the predetermined charging response.

16. The method of claim 1, wherein said detecting comprises detecting when a dV/dt of the capacitor bank reaches a predetermined value.

17. The method of claim 1, wherein said measuring comprises measuring a dV/dt of the capacitor bank during said charging.

18. The method of claim 17, wherein said determining comprises comparing the measured dV/dt to a predetermined dV/dt for the capacitor bank.

19. The method of claim 17, further comprising calculating a capacitance value from the measured dV/dt and a voltage used to charge the capacitor bank, and wherein said determining comprises determining whether the calculated capacitance value is within a predetermined tolerance of a predetermined capacitance value.

20. The method of claim 1, wherein the predetermined charging response is determined during manufacturing of the magnetic device.

21. The method of claim 1, wherein said measuring comprises calculating an average of a plurality of measurements.

22. The method of claim 1, further comprising charging the capacitor bank.

23. A magnetic stimulation device, comprising:
   a magnetic core for generating a magnetic field;
   a power supply;
   a capacitor bank for pulsing the magnetic core, wherein the capacitor bank is charged by the power supply; and
   a processor that measures a charging response of the capacitor bank during charging and determines whether the measured charging response is within a predetermined tolerance of a predetermined charging response.

24. The device of claim 23, further comprising a test resistor, and wherein the processor measures a discharging response of the capacitor bank during discharging of the capacitor bank through the test resistor and determines whether the measured discharging response is within a predetermined tolerance of a predetermined discharging response.

25. The device of claim 23, wherein the processor measures a voltage droop of the capacitor bank during an inactive period and determines whether the measured voltage droop is within a predetermined tolerance of the predetermined voltage droop.

26. The device of claim 23, further comprising a display that provides an alert to a user if said determination is that the measured charging response is not within the predetermined tolerance of the predetermined charging response.

27. The device of claim 24, wherein the display provides an option to modify a power characteristic such that the magnetic field generated by the magnetic core is substantially equivalent to a desired magnetic field.

28. The device of claim 27, wherein the option is to increase a power input to the capacitor bank.

29. The device of claim 28, wherein the increase in power is proportional to a difference between the measured charging response and the predetermined charging response.

30. The device of claim 24, further comprising a communication interface that is operatively coupled to the processor, wherein the communication interface sends a message indicating that the measured charging response of the capacitor bank is out of the predetermined tolerance of the predetermined charging response.

31. The device of claim 30, wherein the communication interface is one of a modem and cable modem.

32. The device of claim 30, wherein the message includes an identification of the magnetic device and an indication of the charging response of the capacitor bank.

33. The device of claim 30, wherein the message is an email message.

34. The device of claim 23, wherein, if the measured charging response is not within the predetermined tolerance of the predetermined charging response, the processor determines an adjustment to make to the operation of the capacitor bank to pulse the magnetic core to generate a magnetic pulse having a desired characteristic.

35. The device of claim 34, wherein the adjustment is increasing a charging voltage during charging of the capacitor bank.

36. The device of claim 23, wherein the processor further permits the capacitor bank to pulse the magnetic core if the processor determined that the measured charging response is within the predetermined threshold of the predetermined charging response.

37. The device of claim 23, wherein the processor measures a dV/dt of the capacitor bank during said charging.

38. The device of claim 37, further comprising a memory that stores a predetermined dV/dt for the capacitor bank, and wherein the processor determines whether the measured charging response is within a predetermined tolerance of a predetermined charging response by comparing the measured dV/dt to the predetermined dV/dt.

39. The device of claim 23, wherein the predetermined charging response is determined during manufacturing of the magnetic device.

40. The device of claim 23, wherein the processor obtains a plurality of measurements and calculates an average of the plurality of measurements.

41. The device of claim 23, further comprising a backup capacitor bank and a switch, wherein the switch is adapted to disconnect the capacitor bank and connect the backup capacitor bank to pulse the magnetic core if the processor determines that the measured charging response is within a predetermined tolerance of a predetermined charging response.

42. A method for monitoring a magnetic device, the method comprising:
    measuring a discharging response of a capacitor bank in a magnetic device during a discharging period, wherein the capacitor bank is adapted to pulse a magnetic core to generate a magnetic field;
    comparing the measured discharging response to a predetermined discharging response;
    determining whether the measured discharging response is within a predetermined tolerance of the predetermined discharging response; and
    in response to whether the measured discharging response is within a predetermined tolerance of the predetermined discharging response, starting, modifying, continuing, or stopping operation of the magnetic device.

43. The method of claim 42, further comprising discharging the capacitor bank through one of a test capacitor and the magnetic core.

44. A method for monitoring a magnetic device, the method comprising:
    measuring a voltage droop of a capacitor bank in a magnetic device during an inactive period, wherein the capacitor bank is adapted to pulse a magnetic core to generate a magnetic field;
    comparing the measured voltage droop to a predetermined voltage droop;
    determining whether the measured voltage droop is within a predetermined tolerance of the predetermined voltage droop; and
    in response to whether the measured voltage droop is within a predetermined tolerance of the predetermined voltage droop, starting, modifying, continuing, or stopping operation of the magnetic device.

45. A magnetic stimulation device, comprising:
    a magnetic core for generating a magnetic field;
    a power supply;
    a capacitor bank for pulsing the magnetic core, wherein the capacitor bank is charged by the power supply;
    a test resistor; and
    a processor that measures a discharging response of the capacitor bank during discharging of the capacitor bank through the test resistor and determines whether the measured discharging response is within a predetermined tolerance of a predetermined discharging response.

46. A magnetic stimulation device, comprising:
    a magnetic core for generating a magnetic field;
    a power supply;
    a capacitor bank for pulsing the magnetic core, wherein the capacitor bank is charged by the power supply; and
    a processor that measures a voltage droop of the capacitor bank during an inactive period and determines whether the measured voltage droop is within a predetermined tolerance of the predetermined voltage droop.

* * * * *